| United States Patent [19] | [11] | 4,183,933 |
|---|---|---|
| Björk et al. | [45] | Jan. 15, 1980 |

[54] DIARYLBUTYL OCTAHYDROPYRAZINOPYRIMIDINONES AND METHODS OF MEDICAL TREATMENT USING THEM

[75] Inventors: Anders K. K. Bjork, Bjärred; Aina L. Abramo; Sven E. H. Hernestam, both of Malmö; Bengt E. S. Kjellberg, Staffanstorp, all of Sweden

[73] Assignee: AB Ferrosan, Malmo, Sweden

[21] Appl. No.: 938,041

[22] Filed: Aug. 30, 1978

[30] Foreign Application Priority Data

Sep. 5, 1977 [GB] United Kingdom ............... 36904/77

[51] Int. Cl.$^2$ ................. C07D 487/04; A61K 31/505
[52] U.S. Cl. .................................... 424/251; 544/279; 544/336; 544/389; 544/384; 544/400; 544/402
[58] Field of Search .......................... 544/279; 424/251

[56] References Cited

U.S. PATENT DOCUMENTS

| 3,560,503 | 2/1971 | Anand et al. ..................... 424/251 X |
| 3,752,816 | 8/1973 | Cooke et al. .......................... 544/279 |
| 3,922,275 | 11/1975 | Noda et al. .......................... 544/279 |
| 3,965,257 | 6/1976 | Carr et al. ............................. 424/45 |
| 4,009,166 | 2/1977 | Noda et al. .......................... 544/279 |

OTHER PUBLICATIONS

Sturm, et al., Chemical Abstracts, vol. 87, 127003e (1977).

*Primary Examiner*—Alton D. Rollins
*Assistant Examiner*—Diana G. Rivers
*Attorney, Agent, or Firm*—Haseltine, Lake & Waters

[57] ABSTRACT

2,3,4,7,8,9-Substituted octahydropyrazinopyrimidinones and acid addition salts thereof. A process for the preparation of said compounds. A pharmaceutical composition comprising such a compound and a conventional carrier. A process for the preparation of said composition. Method of medical treatment of human beings and animals using such compounds.

8 Claims, No Drawings

DIARYLBUTYL OCTAHYDROPYRAZINOPYRIMIDINONES AND METHODS OF MEDICAL TREATMENT USING THEM

This invention relates to a novel class of 2,3,4,7,8,9-substituted octahydropyrazinopyrimidinones, acid addition salts thereof, pharmaceutical compositions containing the same, and methods of making and using the same. The novel octahydropyrazinopyrimidinones according to the invention may be structurally represented by the general formula I

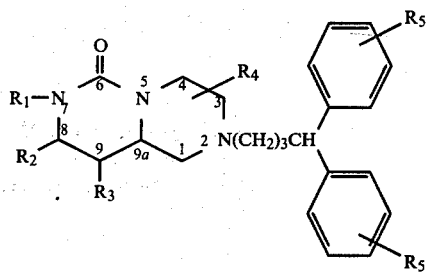

wherein $R_1$ is a member selected from the group of hydrogen, alkyl straight or branch chained having from 1 to 10 carbon atoms, cycloalkyl having from 3 to 8 carbon atoms, aralkyl having from 7 to 9 carbon atoms, phenyl unsubstituted or substituted by one to three substituents selected from halogen, including F, Cl and Br, lower alkyl having from 1 to 5 carbon atoms, lower alkoxy having from 1 to 5 carbon atoms, alkylenedioxy having from 1 to 3 carbon atoms, —$CF_3$ and —CN groups, $R_2$ and $R_3$ are members independently selected from hydrogen, lower alkyl having from 1 to 3 carbon atoms and phenyl unsubstituted or substituted by halogen, including F, Cl and Br. lower alkyl having from 1 to 3 carbon atoms, lower alkoxy having from 1 to 3 carbon atoms, lower thioalkyl having from 1 to 3 carbon atoms and —$CF_3$ groups, $R_4$ is a member selected from the group of hydrogen, lower alkyl having from 1 to 5 carbon atoms and phenyl, and $R_5$ is a member selected from hydrogen, halogen including F, Cl and Br, methoxy and —$CF_3$ groups.

According to the present invention the novel compounds of general formula I are prepared according to the following reaction sequence:

Sequence A by reacting an octahydropyrazinopyrimidinone of formula II

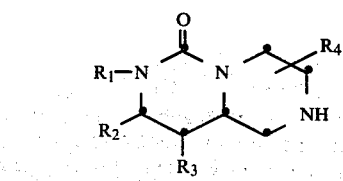

with a 4-substituted-1,1-diarylbutane of formula III

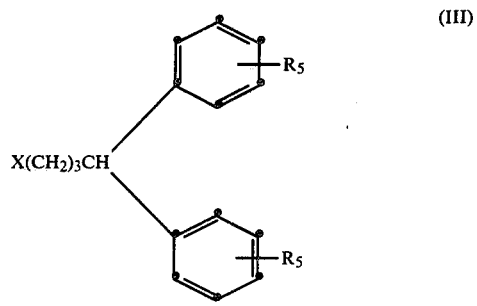

wherein X is selected from the group consisting of halogen, e.g. Cl, Br and I, and another reactive group, e.g. a mesyl and tosyl ester group, to produce a compound of formula I.

The octahydropyrazinopyrimidinones of formula II which are employed in the method of the invention can be prepared by a sequence of reactions according to any of the following:

Sequence B (a)

a Mannich reaction between unsubstituted or substituted methylpyrazine, aqueous formaldehyde and dimethylamine hydrochloride to form a Mannich base of formula IV

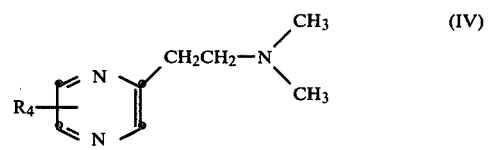

which is quaternized by reaction with methyl iodide to give β-pyrazylethyltrimethylammonium iodide of formula V

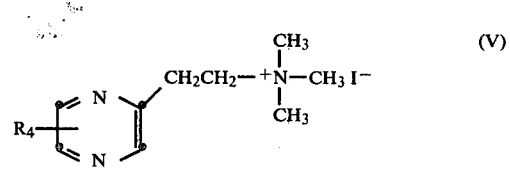

The quaternary compound of formula V is converted to vinylpyrazine of formula VI

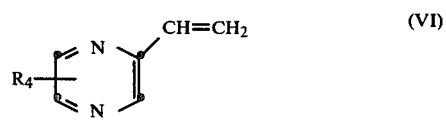

$R_4$ in formulas IV, V and VI being as above defined, by treatment with aqueous sodium hydroxide.

A method for the preparation of α-vinyl substituted analogues of compound of formula VI consists in starting from compound of formula IV, metalating the α-position of the side chain by using lithium diisopropylamide in tetrahydrofuran and then effecting alkylation using alkyl halides $R_3$—X wherein X is selected from the group consisting of Br and I to give the compound of formula VII

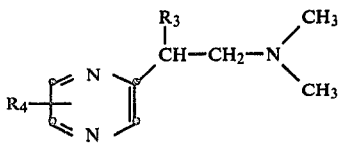

The compound of formula VI is condensed with an amine of formula $R_1$—$NH_2$. The reaction is effected in the presence of an acidic catalyst (methanolic acetic acid) at atmospheric pressure or in a pressure bottle depending on the boiling point of the amine, to give a pyrazylethylated amine of formula VIII

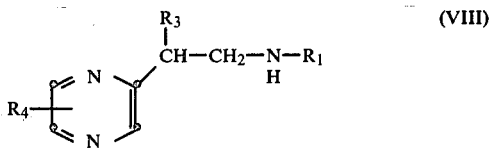

$R_1$, $R_3$ and $R_4$ in formulas VII and VIII being as above defined.

This synthesis of the compound of formula VIII is effected according to Singerman, G. M. and Levine, R., J. Heterocyclic chem., 1, 151 (1964).

Another method for the preparation of the compound VIII consists in the treatment of methylpyrazine with sodium amide in liquid ammonia followed by the addition of aliphatic or aromatic esters of formula $R_2$—$CO_2CH_3$, to give the corresponding pyrazyl methyl ketone of formula IX

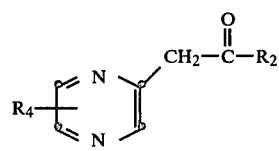

This synthesis of the compound of formula IX is effected according to Behun, J. D. and Levine, R., J. Am. Chem. Soc., 81, 5157 (1959).

The compound of formula IX is reacted with an amine of formula $R_1$—$NH_2$ in a conventional manner to form an azomethine of formula X

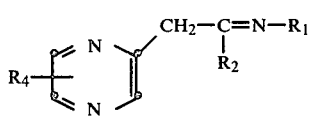

$R_1$, $R_2$ and $R_4$ in formulas IX and X being as above defined, which is reduced by known methods, such as by selective catalytic hydrogenation using nobel metal catalysts or by reducing agents, such as lithium aluminium hydride and the like, in a suitable organic solvent to form a substituted analogue of the compound of formula VIII.

A further method to produce a substituted analogue of the compound of formula VIII is by interaction of an α-haloether of formula XI

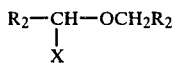

wherein X is selected from the group consisting of Cl and Br, with pyrazylmethylsodium of formula XII

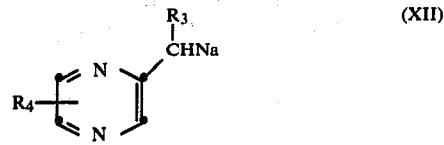

which is prepared from unsubstituted or substituted methylpyrazine and sodium amide in liquid ammonia, to produce an ether of formula XIII

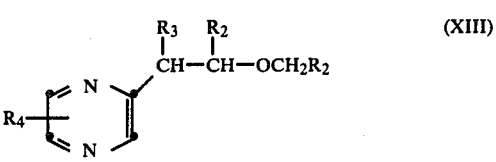

and conversion of the compound of formula XIII to a compound of type VIII by known methods, such as by first reacting compound XIII with HBr in acetic acid to produce a bromide of formula XIV

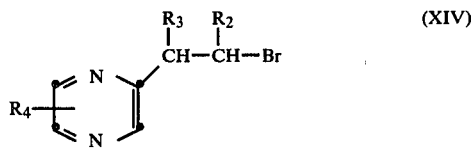

and then reacting the compound of formula XIV with an amine of formula $R_1$—$NH_2$ in a conventional manner to form a substituted analogue of the compound of formula VIII, wherein $R_1$, $R_2$ and $R_3$ are as above defined.

The compound of formula VIII is dissolved in a suitable solvent, e.g. benzene or toluene, and reacted with ethyl chloroformate in the presence of an acid binding agent, e.g. triethylamine, to produce an urethan of formula XV

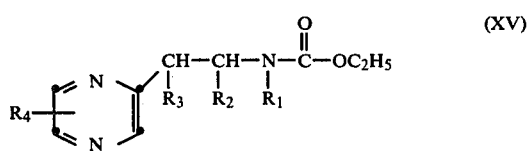

which is hydrogenated over a platinum catalyst to give a compound of formula XVI

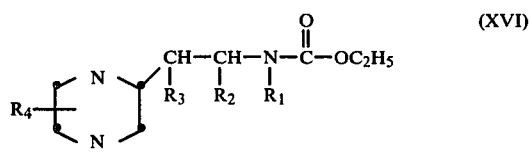

wherein $R_1$-$R_4$ are as above defined.

The compound of formula XVI is cyclized with an alkali metal alkoxide, e.g. sodium methoxide, ethoxide or butoxide, in the presence of a lower alcohol, e.g., methanol, ethanol or butanol, in an autoclave at 75°-150° C. to form a compound of formula II.

Sequence B (b)

a Michael reaction between N-benzylethylenediamine and N-alkylmaleamic acid of formula XVII

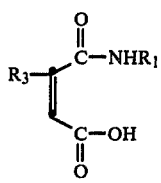

(XVII)

in dioxane to form an amide of formula XVIII

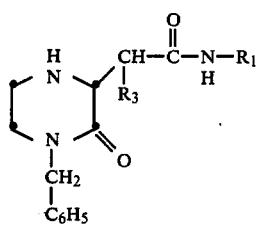

(XVIII)

which is reduced with lithium aluminium hydride in the presence of an inert organic solvent, e.g. tetrahydrofuran, ether and the like to give a compound of formula XIX

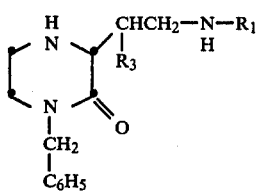

(XIX)

The compound of formula XIX is treated with ethyl chloroformate in an acid medium at about 0° C. to form a monourethan of formula XX

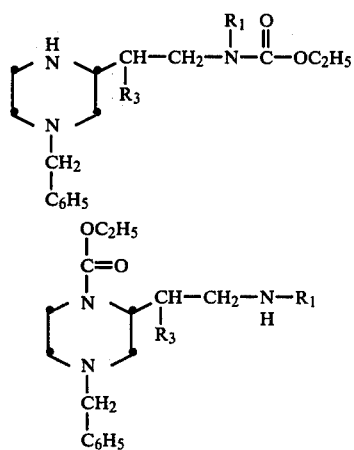

(XXa)

(XXb)

which is cyclized with an alkali metal alkoxide, e.g., sodium methoxide or ethoxide, in the presence of a lower alcohol, e.g. methanol or ethanol, in an autoclave at 75°–150° C. to produce a compound of formula XXI

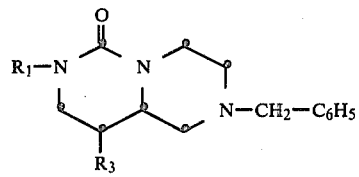

(XXI)

$R_1$ and $R_3$ in formulas XVII, XVIII, XIX, XX and XXI being as above defined.

The compound of formula XXI is hydrogenated over a palladium catalyst to give the compound of formula II.

This synthesis of compound II is effected according to Satyavan Sharma et al., J. Med. Chem., 18, 913 (1975).

In sequence A, the compound of formula II is reacted with a compound of formula III in a suitable solvent, e.g. ethanol, isobutyl acetate, 2-butanone, toluene and the like. The reaction is preferably performed in the presence of an acid binding agent, e.g. sodium carbonate, triethylamine and the like, and advantageously but not necessarily in an autoclave at 75°–150° C., to give the compound of formula I.

It is obvious from formula I that the compounds are racemic and, consequently, the resolution and isolation of the corresponding (+) and (−) forms of stereochemical optical isomers (enantiomorphs) can be accomplished by conventional techniques. Said enantiomorphs are embraced by this invention.

The compounds of formula I may be converted to the therapeutically active non-toxic acid addition salt form by treatment with an appropriate acid, e.g. an inorganic acid, such as a hydrohalic acid, especially hydrochloric and hydrobromic acid, or sulfuric acid, nitric acid, phosphoric acid and the like, or an organic acid, such as acetic, propionic, glycolic, lactic, malonic, succinic, fumaric, tartaric, citric and the like acids. Conversely, the salt form can be converted to the free base form by treatment with alkali.

The new compounds of formula I and the therapeutically active acid addition salts thereof influence mechanisms within the central nervous system. They have been found to inhibit aggressive behaviour in isolated male mice, furthermore some of them inhibit the spontaneous killing by muricidal rats. The compounds block conditioned avoidance behaviour to a varying degree. They have an enhancing effect on brain integrative mechanisms, e.g. increased arousal reactions without inducing addiction. In tests on monkeys the compounds have, depending on the dose, an alerting effect on defined behavioural parameters; at higher doses some of them also have a sedative effect. The compounds also give a favourable effect on the gastric function. Furthermore, selected compounds have analgetic, anti-inflammatory and anorexigenic properties and some of them have useful cardiac and vascular properties. The compounds also influence the hypothalamic hormonal regulation. Their toxicity is very low.

Effective quantities of any of the foregoing pharmacologically active compounds of formula I may be administered to a human being or animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier or excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards, preferably 25, 50, or 100 milligrams or even higher depending on the condition to be treated and the age and weight of the patient as well as the response to the medication.

The unit dose may be from 1 to 200 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician or veterinarian.

The following formulations are representative for all of the pharmacologically active compounds of this invention.

Example of a suitable capsule formulation:

|  | per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

|  | per tablet, mg |
|---|---|
| Active ingredient, as salt | 10 |
| Potato starch | 90 |
| Colloidal silica | 10 |
| Talc | 20 |
| Magnesium stearate | 2 |
| 5% Aqueous solution of gelatin | 25 |
| Total | 157 |

The pharmaceutical preparations may also contain therapeutically useful substances other than the pharmacologically active compounds of formula I.

The following examples are intended to illustrate the present invention, without limiting the scope thereof.

EXAMPLE 1

β-Dimethylaminoethylpyrazine

A mixture of 94.0 g (1.0 mole) of methylpyrazine and 83.9 g (1.03 mole) of dimethylamine hydrochloride was heated until it began refluxing. 131.3 g (40% aqueous solution) (1.75 mole) of formaldehyde was added over a period of two hours. The resulting brown viscous mass was refluxed for additional 2.5 hours. The mixture was cooled to room temperature. It was diluted with 250 ml of water, made basic with 10% sodium hydroxide solution and extracted with chloroform. After removing the chloroform the residue was distilled to give 100.6 g of β-dimethylaminoethylpyrazine, b.p. 116°–120° C. at 20 mm Hg.

EXAMPLE 2

Vinylpyrazine

The quaternary compound formed from the reaction of 90.6 g (0.6 mole) of β-dimethylaminoethylpyrazine and 90.0 g (0.64 mole) of methyl iodide was extracted with 450 ml of water. 24.0 g (0.6 mole) of sodium hydroxide was added and the mixture was refluxed for 1 hour. The mixture was cooled to room temperature and extracted with several portions of methylene chloride. After the combined extracts were dried over sodium sulphate the methylene chloride was removed by distillation at atmospheric pressure. The residue was distilled to give 54.8 g of vinylpyrazine, b.p. 64°–68° C. at 22 mm Hg.

EXAMPLE 3

2-(β-Dimethylaminoethyl)-5-methylpyrazine

A mixture of 75.0 g (0.7 mole) of 2,5-dimethylpyrazine and 41.0 g (0.5 mole) of dimethylamine hydrochloride was heated at 140° C. 60.0 g (38% aqueous solution) (0.75 mole) of formaldehyde was added over a period of two hours. After two hours additional heating the mixture was cooled. It was diluted with 110 ml of water, made basic with 10% sodium hydroxide and extracted with chloroform. The solvent was removed and the residue distilled to give 28.6 g of 2-(β-dimethylaminoethyl)-5-methylpyrazine, b.p. 106°–110° C. at 10 mm Hg.

EXAMPLE 4

2-Vinyl-5-methylpyrazine

The procedure of Example 2 was repeated, starting with 2-(β-dimethylaminoethyl)-5-methylpyrazine to form 2-vinyl-5-methylpyrazine, b.p. 79°–81° C. at 20 mm Hg.

EXAMPLE 5

β-Dimethylamino-α-methylethylpyrazine

To 0.56 mole of lithium diisopropylamide, prepared from n-butyllithium and diisopropylamine in tetrahydrofuran, was added at −10° C. 84.6 g (0.56 mole) of β-dimethylaminoethylpyrazine in 1200 ml of tetrahydrofuran over a period of 30 minutes. The reaction mixture was stirred for additional 30 minutes. The deep red-coloured reaction mixture was cooled to −30° C. and 95.4 g (0.56 mole) of methyl iodide was added over a period of 20 minutes and the reaction mixture was stirred for three additional hours at room temperature. The mixture was poured onto ice and extracted with ether. The combined extracts were dried over sodium sulphate and the ether removed by distillation. The residue was distilled to give 91.0 g of β-dimethylamino-α-methylethylpyrazine, b.p. 90°–93° C. at 9 mm Hg.

EXAMPLE 6

α-Methylvinylpyrazine

The procedure of Example 2 was repeated starting with β-dimethylamino-α-methylethylpyrazine to give α-methylvinylpyrazine, b.p. 62°–66° C. at 10 mm Hg.

EXAMPLE 7

β-Ethylaminoethylpyrazine

A mixture of 21.2 g (0.2 mole) of vinylpyrazine, 18.0 g (0.4 mole) of ethylamine, 6.0 g (0.1 mole) of acetic acid and 60 ml methanol was placed in a pressure bottle and heated at 70° C. for 24 hours. After removing the methanol, the residue was made basic with 8.0 g (0.2 mole) of sodium hydroxide in 80 ml of water and extracted with several portions of chloroform. After removing the chloroform, the residue was distilled to give 24.5 g of β-ethylaminoethylpyrazine, b.p. 70°-72° C. at 0.5 mm Hg, $n_D^{25} = 1.5103$.

EXAMPLE 8

β-(N-Ethoxycarbonylethylamino)ethylpyrazine

To a solution of 30.2 g (0.20 mole) of β-ethylaminoethylpyrazine in 240 ml of benzene and 56 ml (0.40 mole) of triethylamine was added dropwise over a period of 15 minutes 22.9 g (0.21 mole) of ethyl chloroformate. The mixture was refluxed for 1 hour. It was filtrated and the filtrate concentrated under vacuum. The residue was distilled to give 38.8 g of β-(N-ethoxycarbonylethylamino-ethylpyrazine, b.p. 100°-105° C. at 0.1 mm Hg.

EXAMPLE 9

β-(N-Ethoxycarbonylethylamino)-ethylpiperazine 22.3 g (0.10 mole) of β-(N-ethoxycarbonylethylamino)ethylpyrazine dissolved in 300 ml of ethanol and 28.6 ml (0.50 mole) of acetic acid was treated with hydrogen over a platinum catalyst in a Parr hydrogenator at 2.5–3 atm. The mixture was made basic with 22 g (0.55 mole) of sodium hydroxide in 200 ml of water. The ethanol was removed under reduced pressure and the residue extracted with methylene chloride. The extracts were dried over sodium sulfate. Removal of the methylene chloride gave crude β-(N-ethoxycarbonylethylamino)-ethylpiperazine. Yield 21.3 g.

EXAMPLE 10

7-Ethyloctahydro-6H-pyrazino[1,2-c]pyrimidin-6-one 20.6 g (0.09 mole) of β-(N-ethoxycarbonylethylamino)-ethylpiperazine was added to a solution of sodium ethoxide prepared from 2.53 g (0.11 mole) of sodium in 120 ml of ethanol. The mixture was refluxed for 36 hours. The solution was concentrated in vacuum and the residue taken up in water and extracted with methylene chloride. The methylene chloride solution was dried over sodium sulfate and concentrated. The residue was distilled to give 12.9 g of the title compound, b.p. 115°-120° C. at 0.01 mm Hg. The hydrochloride had the melting point 215°-217° C.

EXAMPLE 11

7-Methyloctahydro-6H-pyrazino[1,2-c]pyrimidin-6-one hydrobromide

The procedure of Example 10 was repeated starting with β-(N-ethoxycarbonylmethylamino)-ethylpiperazine. The title compound so obtained had the melting point 225°-227° C.

NMR spectrum (chemical shifts and coupling constants) of 7-methyloctahydro-6H-pyrazino[1,2-c]pyrimidin-6-one hydrobromide[a].

| Hydrogen | Chemical shift σ (ppm) | Coupling constants \|J (Hz)\| | | |
|---|---|---|---|---|
| 1 A | 2,74 | $J_{1A1B}$ 12 | $J_{1A9a}$ 11,5 | |
| 1 B | (b) | $J_{1B9a}$ 3 | | |
| 3 A | 2,86 | $J_{3A3B}$ 12,7 | $J_{3A4A}$ 12,5 | $J_{3A4B}$ 3,3 |
| 3 B | 3,30 | $J_{3B4A}$ 3,1 | $J_{3B4B}$ 2,3 | |
| 4 A | 2,92 | $J_{4A4B}$ 14,4 | | |
| 4 B | 4,32 | | | |
| $CH_3$—N | 2,81 | | | |
| 8 A | (b) | $J_{8A8B}$ (b) | $J_{8A9A}$ 9,5 | $J_{8A9B}$ 4 |
| 8 B | (b) | $J_{8B9A}$ 5,5 | $J_{8B9B}$ 4 | |
| 9 A | 1,71 | $J_{9A9B}$ 13,5 | $J_{9A9a}$ 9,5 | |
| 9 B | 2,03 | $J_{9B9a}$ 5 | | |
| 9 a | 3,65 | | | |

(a) Measured at 270 MHz in DMSO-$d_6$, with tetramethylsilane as internal reference.
(b) Signal obscured, not analysed.

EXAMPLE 12

7-Ethyloctahydro-2-[4,4-(di-p-fluorophenyl)butyl]-6H-pyrazino[1,2-c]pyrimidin-6-one hydrochloride A stirred mixture of 11.0 g (0.06 mole) of 7-ethyloctahydro-6H-pyrazino[1,2-c]pyrimidin-6-one, 19.7 g (0.07 mole) of 4-chloro-1,1-(di-p-fluorophenyl)-butane, 12.0 g of anhydrous sodium carbonate, 100 mg of potassium iodide and 300 ml of isobutyl acetate was heated at reflux for 40 hours. The mixture was filtered and the filtrate concentrated under vacuum. The residual oil was dissolved in ethanol and the hydrochloride was precipitated with ethanolic HCl. The solid was collected by filtration and recrystallized from isopropanol to give 21.4 g of the title compound. Melting point 189°-190° C. Melting points of compounds obtained according the above examples and analoguous procedures are summarised in Tables I and II.

Table 1

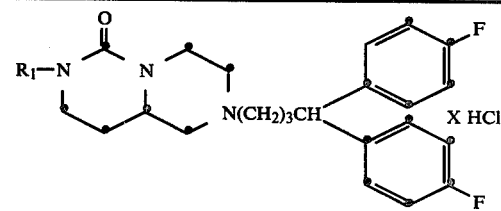

| $R_1$ | M.p., °C.[a] |
|---|---|
| H | 260–262 |
| $CH_3$ | 221–223 |
| $C_2H_5$ | 189–190 |
| n-$C_3H_7$ | 181–183 |
| iso-$C_3H_7$ | 168–170[b] |
| cyclo-$C_3H_5$ | 191–193 |
| n-$C_4H_9$ | 173–174 |
| iso-$C_4H_9$ | 138–139 |
| n-$C_5H_{11}$ | 166–167 |
| iso-$C_5H_{11}$ | 170–172 |
| cyclo-$C_5H_9$ | 134–136 |
| n-$C_6H_{13}$ | 168–170 |
| cyclo-$C_6H_{11}$ | 162–164 |
| n-$C_8H_{17}$ | 147–149 |
| $C_6H_5$ | 124–125[c] |
| p-$CH_3C_6H_4$ | 144–146[c] |

Table 1-continued

R$_1$ structure with N(CH$_2$)$_3$CH group and difluorophenyl substituents × HCl

| R$_1$ | M.p., °C.[a] |
|---|---|
| C$_6$H$_5$CH$_2$ | 101–103[d] |

[a] Melting points are uncorrected
[b] Oxalate salt
[c] Free base
[d] HCl salt, dihydrate

Table II

C$_2$H$_5$—N structure with R$_3$, R$_4$ substituents, N—(CH$_2$)$_3$—CH and difluorophenyl groups × HCl

| R$_3$ | R$_4$ | M.p., °C.[a] |
|---|---|---|
| CH$_3$ | H | 249–251 |
| H | CH$_3$ | 198–200 |

[a] Melting points are uncorrected.

We claim:

1. A compound of the general formula I

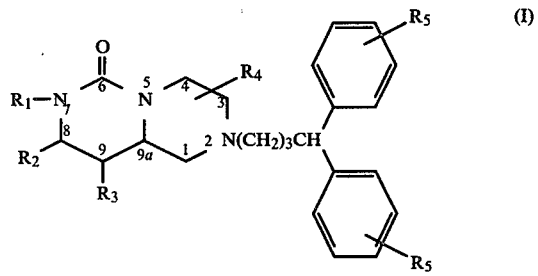

(I)

wherein R$_1$ is a member selected from the group consisting of hydrogen, straight and branch chained alkyl containing from 1 to 10 carbon atoms, cycloalkyl containing from 3 to 8 carbon atoms, aralkyl containing from 7 to 9 carbon atoms, phenyl unsubstituted or substituted by one to three substituents selected from halogen, including F, Cl and Br, lower alkyl containing from 1 to 5 carbon atoms, lower alkoxy containing from 1 to 5 carbon atoms, alkylenedioxy having from 1 to 3 carbon atoms, —CF$_3$ and —CN groups, R$_2$ and R$_3$ are members independently selected from hydrogen, lower alkyl containing from 1 to 3 carbon atoms and phenyl unsubstituted or substituted by halogen including F, Cl and Br, lower alkyl containing from 1 to 3 carbon atoms, lower alkoxy containing from 1 to 3 carbon atoms, lower thioalkyl containing from 1 to 3 carbon atoms and —CF$_3$ groups, R$_4$ is a member selected from the group consisting of hydrogen, lower alkyl containing from 1 to 5 carbon atoms and phenyl, and R$_5$ is a member selected from the group consisting of hydrogen, halogen including F, Cl and Br, methoxy and —CF$_3$ groups, and acid addition salts thereof.

2. A compound of claim 1 wherein R$_1$ is selected from the group consisting of hydrogen and alkyl containing from 1 to 10 carbon atoms.

3. A compound of claim 1 wherein R$_1$ is cycloalkyl containing from 3 to 8 carbon atoms.

4. A method of treating human beings and animals suffering from mental illness, neurosis and behavioural disturbances by administering a compound of formula I as defined in claim 1.

5. A method of treating human beings and animals for analgesic and anti-inflammatory purposes by administering a compound of formula I as defined in claim 1.

6. A method of treating human beings and animals for anorexigenic purposes by administering a compound of formula I as defined in claim 1.

7. A method of treating human beings and animals suffering from cardiac and vascular disorders by administering a compound of formula I as defined in claim 1.

8. A pharmaceutical composition for treatment of mental illness, neurosis, behavioral disturbances, inflammation, anorexia or cardiac and vascular disorders, containing a pharmaceutically effective amount of a compound of Formula I as defined in claim 1, in a conventional pharmaceutical carrier.

* * * * *

UNITED STATES PATENT AND TRADEMARK OFFICE
CERTIFICATE OF CORRECTION

PATENT NO. : 4,183,933
DATED : January 15, 1980
INVENTOR(S) : Bjork et al

It is certified that error appears in the above-identified patent and that said Letters Patent are hereby corrected as shown below:

In Column 3, first formula, change "(VIII)" to --(VII)--

Column 5, formula (XIX), amend to read:

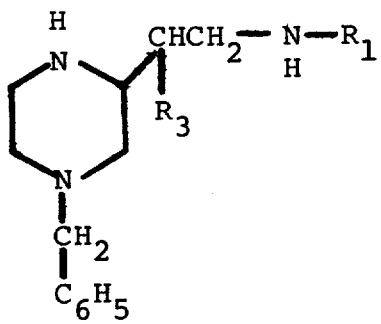

Signed and Sealed this

Second Day of February 1982

[SEAL]

Attest:

GERALD J. MOSSINGHOFF

Attesting Officer

Commissioner of Patents and Trademarks